United States Patent
Kimball et al.

(10) Patent No.: US 6,534,536 B1
(45) Date of Patent: Mar. 18, 2003

(54) ALKYLSULFONAMIDO HETEROCYCLIC THROMBIN INHIBITORS

(75) Inventors: Spencer D. Kimball, E. Windsor, NJ (US); Jagabandhu Das, Mercerville, NJ (US); Wan Fang Lau, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/213,964

(22) Filed: Mar. 16, 1994

(51) Int. Cl.$^7$ ............... A61K 31/40; C07D 207/22
(52) U.S. Cl. ............ 514/423; 514/212; 514/261; 514/303; 514/345; 514/350; 514/354; 540/604; 540/605; 540/607; 544/264; 546/119; 546/216; 546/220; 546/221; 546/223; 546/226; 548/537; 548/538
(58) Field of Search ............... 546/119, 216, 546/220, 221, 223, 226; 540/604, 605, 607; 548/537, 538; 514/212, 261, 345, 303, 350, 354, 423; 544/264

(56) References Cited

U.S. PATENT DOCUMENTS

| | | | |
|---|---|---|---|
| 4,258,192 A | 3/1981 | Okamoto et al. | 546/166 |
| 4,346,078 A | 8/1982 | Bajusz et al. | 424/177 |
| 4,904,661 A | 2/1990 | Pilgrim et al. | 514/237.5 |
| 5,002,964 A | 3/1991 | Loscalzo | 514/423 |
| 5,561,146 A | * 10/1996 | Kimball et al. | 514/326 |
| 5,583,146 A | * 12/1996 | Kimball et al. | 514/326 |

FOREIGN PATENT DOCUMENTS

| EP | 559046 | * 9/1993 |
|---|---|---|
| WO | WO9311152 | 6/1993 |

OTHER PUBLICATIONS

Larsen et al. "Prodrug forms for the sulfonamide group . . . " Ca 111:45121 (1989).*
Shyam et al "Dis(aylsulfonyl) Hydrazine." J. Med. Chem. 29 1323–1325 (1986).*
Banner et al "Serine Profease: 3D Structures, Mechanism" Perspect. Med. Chem. Bernard Eds. Verlag Publishing. p. 27–43 (1993).*
Burger "A Guide to the Chemical Basis of Dry Design" Wiley Science, p. 15 (1984).*
Hackh's Chemical Dictionary, McGraw Hill, p. 16 (1982).*
McOmie "Protective groups in Organic Chemistry" Pleumann Press, p. 46–73 (1974).

Bajnasz et al "Highly Selective Autaevapalants . . . " J. Med. Chem. 33 1729–35 (1990).
Schuman et al "Highly Selective Tripeptide Thrombin Inhibitors" J. Med Chem. 36 314–319 (1993).
Spatola et al "Amide Bond Surrogates" Tetrahedron, 44 821–833 (1988).
Rubini et al "Synthesis Of Isosteric Methylene–oxy . . . " Tetrahedron 42 6039–6045 (1986).*
Robert M. Knabb et al, "In Vivo Characterization of a New Synthetic Thrombin Inhibitor," Thrombosis and Hemostasis (1992) 67, 56–59.
Charles V. Jackson et al, "Pharmacological Assessment of the Antithrombotic Activity of the Peptide Thrombin Inhibitor, D–Methyl–Phenylalanyl–Prolyl–Arginal (GYKI–14766), in a Canine Model of Coronary Artery Thrombosis," J. Pharm. Exp. Ther. (1992) 261, 546–552.

* cited by examiner

Primary Examiner—Ceila Chang
(74) Attorney, Agent, or Firm—Burton Rodney

(57) ABSTRACT

Alkylsulfonamido heterocyclic thrombin inhibitors are provided which have the structure

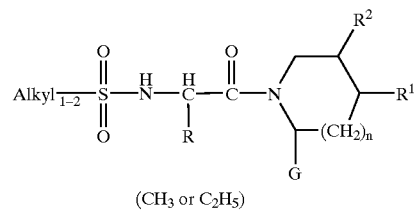

wherein G is

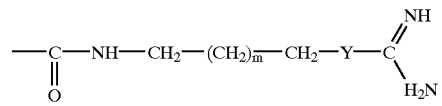

wherein
n is 0, 1 or 2 or 3; m is 0, 1, 2 or 3; Y is NH or S;
R is hydrogen, hydroxyalkyl, aminoalkyl, alkyl, cycloalkyl, amidoalkyl, arylalkyl, alkenyl, aryl, alkynyl, arylalkoxyalkyl, or an amino acid side chain;
$R^1$ and $R^2$ are independently hydrogen, lower alkyl, cycloalkyl, aryl, hydroxy, alkoxy, oxo, thioketal, thioalkyl, thioaryl, amino or alkylamino; or $R^1$ and $R^2$ can be taken together with the carbons to which they are attached to form a cycloalkyl, aryl or heteroaryl ring.

7 Claims, No Drawings

ALKYLSULFONAMIDO HETEROCYCLIC THROMBIN INHIBITORS

FIELD OF THE INVENTION

The present invention relates to alkylsulfonamido heterocyclic compounds which are thrombin inhibitors and thus useful in inhibiting formation of thrombi.

BACKGROUND OF THE INVENTION

U.S. application Ser. No. 146,714 filed Nov. 10, 1993, discloses sulfonamido heterocyclic thrombin inhibitors of the invention have the structure

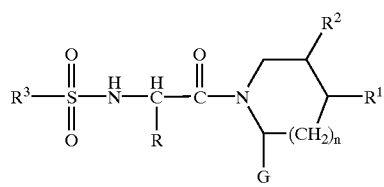

wherein G is an amido moiety which is

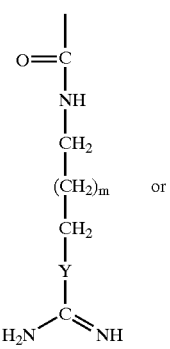

(G1)

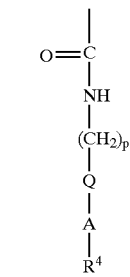

(G2)

including all stereoisomers thereof; and including all pharmaceutically acceptable salts thereof; wherein R is hydrogen, hydroxyalkyl, aminoalkyl, amidoalkyl, alkyl, cycloalkyl, aryl, arylalkyl, alkenyl, alkynyl, arylalkoxyalkyl, or an amino acid side chain, either protected or unprotected;

$R^1$ and $R^2$ are independently hydrogen, lower alkyl, cycloalkyl, aryl, hydroxy, alkoxy, oxo, thioxo thioalkyl, thioaryl, amino or alkylamino; or $R^1$ and $R^2$ together with the carbons to which they are attached form a cycloalkyl, aryl, or heteroaryl ring; and $R^3$ is lower alkyl, aryl, arylalkyl, heteroaryl, quinolinyl or tetrahydroquinolinyl;

n is 0, 1 or 2;
m is 0, 1, 2 or 3;
Y is NH or S;
p is 0, 1 or 2;
Q is a single bond or

A is aryl or cycloalkyl, or an azacycloalkyl ring A of 4 to 8 carbons in the ring or an azaheteroalkyl ring a of 4 to 8 carbons in the ring, A

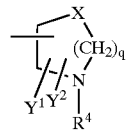

where
X is $CH_2$, O, S or NH;
q is 0, 1, 2, 3 or 4 if x is $CH_2$;
q is 2, 3 or 4 if X is O, S or NH;
$Y^1$ and $Y^2$ are independently H, lower alkyl, halo or keto; and
$R^4$ is guanidine, amidine or aminomethyl;
where A is aryl or cycloalkyl, $R^4$ is guanidine, amidine or aminomethyl;
where A is azacycloalkyl or azaheteroalkyl, $R^4$ is amidine;
provided that where X is a hetero atom (that is, A is azaheteroalkyl), then there must be at least a 2-carbon chain between X and any N atom in the ring A or outside ring A;
and provided that where G is Gl, then if $R^3$ is alkyl, the alkyl must contain at least 3 carbons.

DESCRIPTION OF THE INVENTION

The alkylsulfonamido heterocyclic thrombin inhibitors of the invention have the structure I

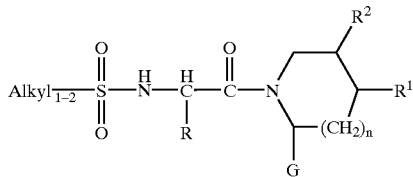

I wherein G is an amido moiety which is

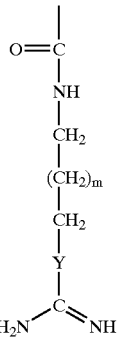

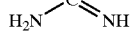

including all stereoisomers thereof; and including all pharmaceutically acceptable salts thereof; wherein R is hydrogen, hydroxyalkyl, aminoalkyl, amidoalkyl, alkyl, cycloalkyl, aryl, arylalkyl, alkenyl, alkynyl, arylalkoxyalkyl, or an amino acid side chain, either protected or unprotected;

$R^1$ and $R^2$ are independently hydrogen, lower alkyl, cycloalkyl, aryl, hydroxy, alkoxy, oxo, thioketal, thioalkyl, thioaryl, amino or alkylamino; or $R^1$ and $R^2$ together with the carbons to which they are attached form a cycloalkyl, aryl, or heteroaryl ring; and n is 0, 1 or 2;

m is 0, 1, 2 or 3;

Y is NH or S; and $Alkyl_{1-2}$ is methyl or ethyl.

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents (for example, to form $CF_3$ or $CF_3CH_2$) and/or 1 or 2 of the following substituents: an aryl substituent (for example, to form benzyl or phenethyl), an alkyl-aryl substituent, a haloaryl substituent, a cyclo-alkyl substituent, an alkylcycloalkyl substituent, an alkenyl substituent, an alkynyl substituent, hydroxy or a carboxy substituent. It will be appreciated that the same "alkyl" group may be substituted with one or more of any of the above substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy groups.

The term "aryl" or "Ar" as employed herein by itself or as part of another group refers to mono-cyclic or bicyclic aromatic groups containing from 6 to 10 carbons in the ring portion, such as phenyl, or naphthyl. Aryl (or Ar), phenyl or naphthyl may include substituted aryl, substituted phenyl or substituted naphthyl, which may include 1 or 2 substituents on either the Ar, phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" as employed herein by itself or as part of another group includes a carbon chain of up to 16 carbons, preferably 3 to 10 carbons, containing one double bond which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein by itself or as part of another group includes a carbon chain of up to 16 carbons, preferably 3 to 10 carbons, containing one triple bond which will be separated from "N" by at least one saturated carbon moiety such as —$(CH2)_{q'}$— where q' can be 1 to 14, such as 2-propynyl, 2-butynyl, 3-butynyl and the like.

The term "heteroaryl" or heteroaromatic by itself or as part of another group refers to a 5–10-membered aromatic ring which includes 1, 2, 3 or 4 hetero atoms such as nitrogen, oxygen or sulfur, such as

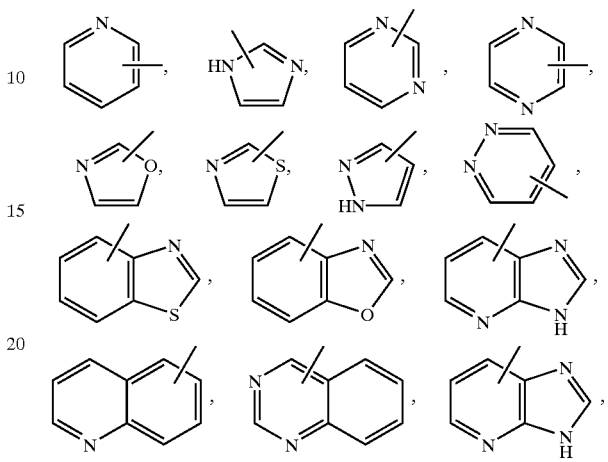

and the like. The heteroaryl rings may optionally be fused to aryl rings defined previously. The heteroaryl rings may optionally include 1 or 2 substituents such as halogen (Cl, Br, F or $CF_3$), lower alkyl, lower alkoxy, carboxy, amino, lower alkylamino and/or dilower alkylamino.

The term "amino acid side chain" refers to any of the known alpha-amino acids such as arginine, histidine, alanine, glycine, lysine, glutamine, leucine, valine, serine, homoserine, allothreonine, naphthylalanine, isoleucine, phenylalanine and the like.

Preferred are compounds of formula I wherein n is 0 or 1; m is 2; $Alkyl_{1-2}$ is methyl; R is arylalkyl; $R^1$ and $R^2$ are independently hydrogen or lower alkyl such as methyl or ethyl; and Y is —NH—.

The compounds of formula I of the invention wherein Y is NH may be prepared according to the following Reaction Sequence I.

Reaction Sequence I

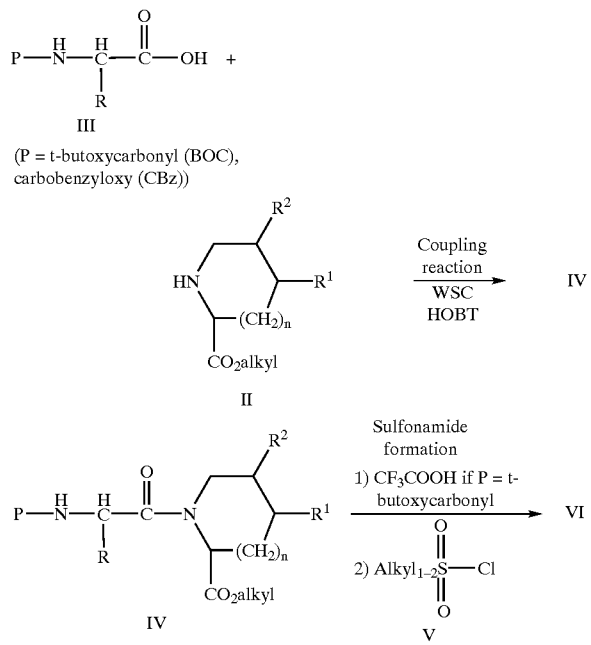

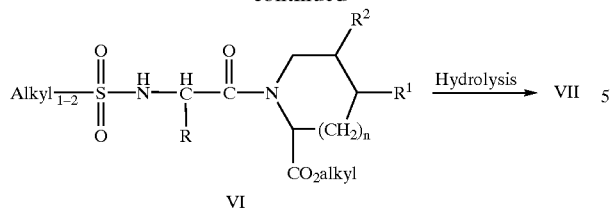
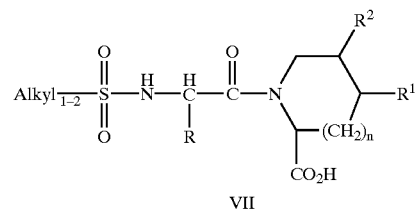
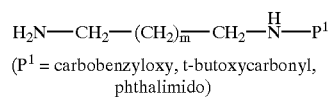
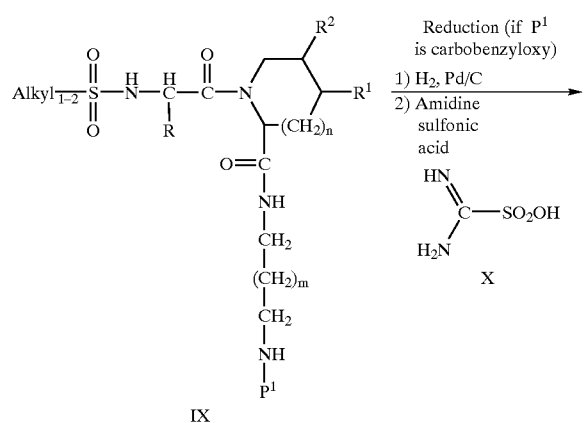
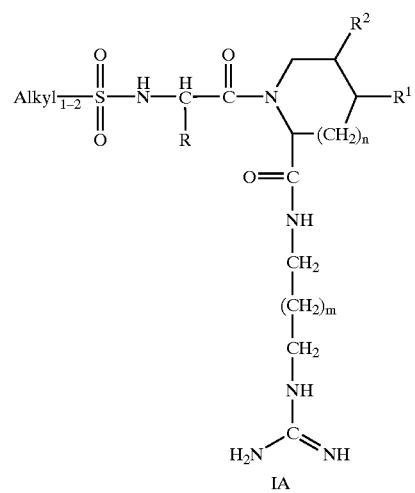
The compounds of formula I of the invention wherein Y is NH may also be prepared according to the following Reaction Sequence II
Reaction Sequence II
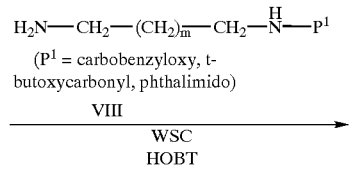
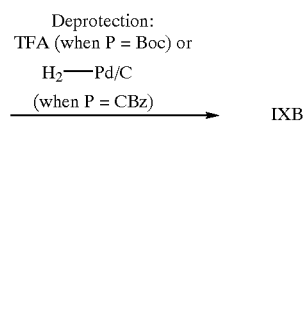
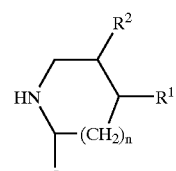
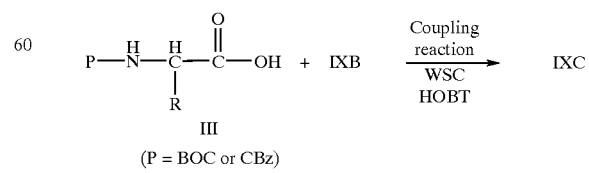

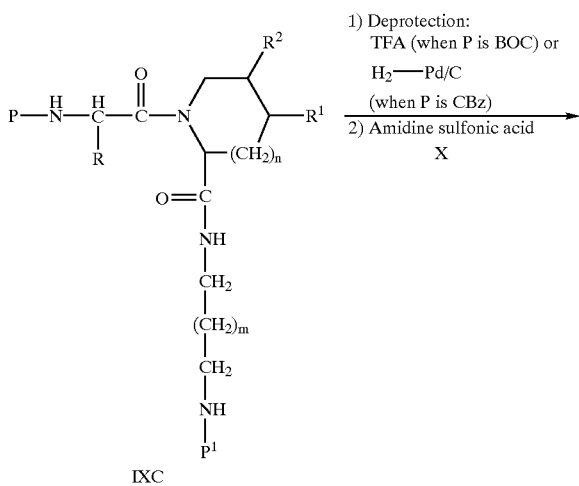

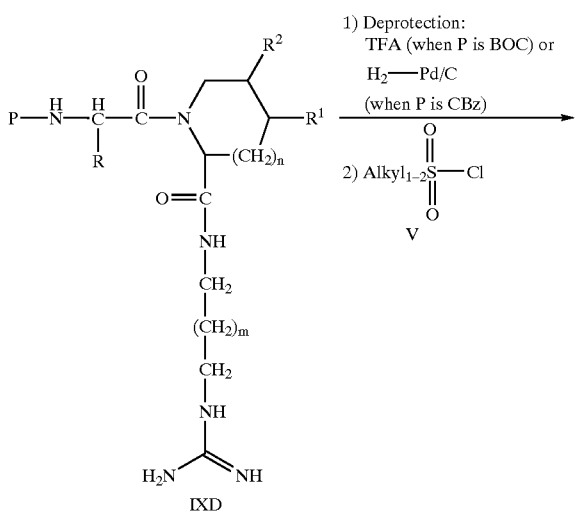

As seen in the above Reaction Sequence I, compounds of formula I wherein Y is —NH—, are prepared as follows. The ester II is made to undergo a carbodiimide coupling reaction with protected amino acid III in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IV. Amide IV is deprotected by treatment with trifluoroacetic acid with or without the presence of dry inert organic solvent such as dichloromethane, chloroform or THF at temperatures within the range of from about −15° to about 20° C. Sulfonyl chloride V is added followed by organic base such as triethylamine, pyridine or N,N-diisopropylethylamine to form the sulfonamide VI. Sulfonamide VI is hydrolyzed by treatment with alkali metal base such as NaOH or LiOH in the presence of an alcohol solvent such as methanol or ethanol. The reaction mixture is acidified with HCl, KHSO$_4$ or H$_2$SO$_4$, to form acid VII. The acid VII is then subjected to a carbodiimide coupling reaction wherein VII is treated with protected amine VIII in the presence of WSC or DCC, and HOBT, and NMM, in the presence of an inert organic solvent such as dimethylformamide, THF or N-methylpyrrolidone, to form sulfonamide IX. The sulfonamide IX is then dissolved in an alcohol solvent such as ethanol or methanol, to which HCl has been added and the mixture is hydrogenated over Pd—C or Pd(OH)$_2$—C in the case where P$^1$ is carbobenzyloxy. The product is then treated with amidine sulfonic acid X in the presence of an alcohol solvent such as ethanol to form the compound of the invention IA.

As seen in the above Reaction Sequence II, compounds of formula I wherein Y is —NH—, are also prepared as follows. The protected acid IIA is made to undergo a carbodiimide coupling reaction with protected diamine VIII in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IXA. Amide IXA is deprotected by treatment with trifluoroacetic acid (TFA) when P is t-butoxycarbonyl (BOC) or H$_2$—Pd/C when P is carbobenzyloxy (CBz), with or without the presence of dry inert organic solvent such as dichloromethane, chloroform or THF, at temperatures within the range of from about −15° to about 20° C. to form amide IXB. The amide IXB is then subjected to a carbodiimide coupling reaction wherein IXB is treated with protected amine III in the presence of WSC or DCC, and HOBT, and NMM, in the presence of an inert organic solvent such as dimethylformamide, THF or N-methylpyrrolidone, to form amide IXC. The amide IXC is then dissolved in an alcohol solvent such as ethanol or methanol, to which HCl has been added and the mixture is hydrogenated over Pd—C or Pd(OH)$_2$—C in the case where P$^1$ is CBz or treated with trifluoroacetic acid when P$^1$ is BOC. The product is then treated with amidine sulfonic acid X in the presence of an alcohol solvent such as ethanol to form IXD. Compound IXD is deprotected by treatment with TFA when P is BOC or by treatment with H$_2$—Pd/C when P is CBz, as described above, and sulfonyl chloride V is added followed by organic base such as triethyl-amine, pyridine or N,N-diisopropylethylamine to form the sulfonamide IA.

The compounds of formula I of the invention wherein Y is S may be prepared according to the following Reaction Sequence III.

Reaction Sequence III

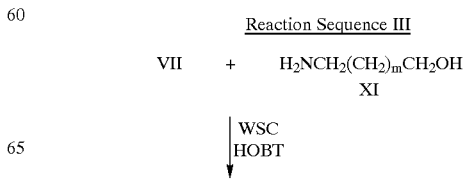

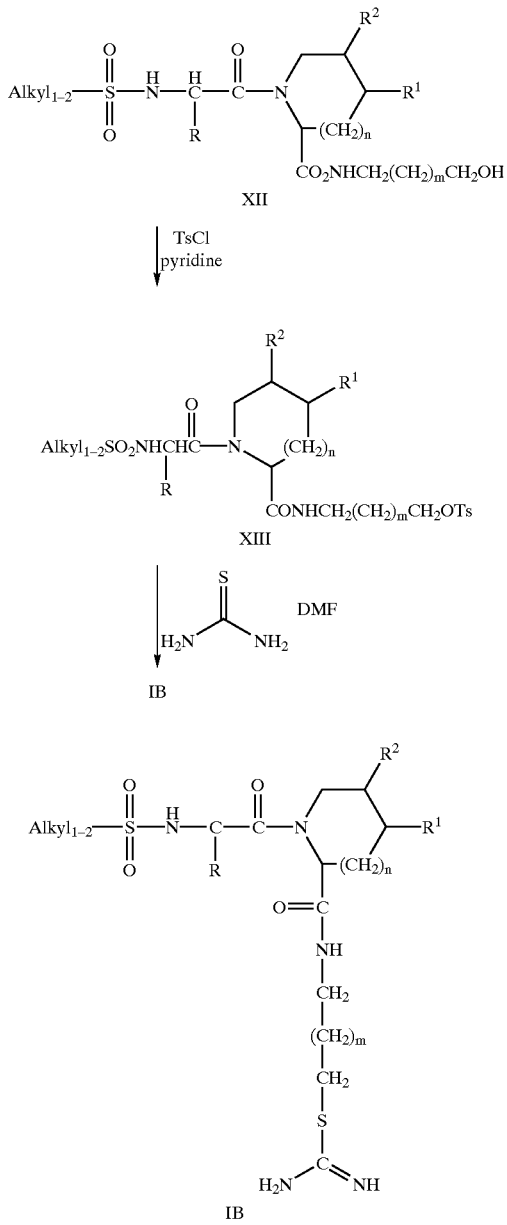

Referring to the above Reaction Sequence III, compounds of formula I wherein Y=S can be prepared as follows. The acid VII is subjected to a carbodiimide coupling reaction wherein VII is treated with an aminoalcohol XI in the presence of WSC or DCC, HOBT, and NMM, in the presence of an inert organic solvent such as dimethylformamide, THF or N-methylpyrrolidone, to form sulfonamide alcohol XII. The sulfonamide alcohol XII is reacted with p-toluenesulfonyl chloride (TsCl) in pyridine, or in a solvent such as methylene chloride or chloroform, with N,N-dimethylaminopyridine to provide toluenesulfonate XIII. The compound IB (Y=S) is prepared by treating XIII with thiourea in a solvent such as DMF or DMSO at temperatures within the range of from about 25° C. to about 100° C.

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like.

The compounds of the present invention are serine protease inhibitors, and in particular may inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), disseminated intravascular coagulopathy (DIC), Kasabach-Merritt syndrome, pulmonary embolism, myocardial infarction, stroke, thromboembolic complications of surgery (such as hip replacement and endarterectomy) and peripheral arterial occlusion. In addition to its effects on the coagulation process, thrombin has been shown to activate a large number of cells (such as neutrophils, fibroblasts, endothelial cells, smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodegenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorpeal blood circuits, such as those necessary in dialysis and surgery (such as coronary artery bypass surgery).

The compounds of the present invention may also be used in combination with thrombolytic agents, such as tissue plasminogen activator (natural or recombinant), streptokinse, urokinase, prourokinase, anisolated streptokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc., as called for by accepted pharmaceutical practice.

The following Examples represent preferred embodiments of the present invention. Unless otherwise indicated, all temperatures are expressed in degrees Centigrade.

EXAMPLE 1

N-[4-[(Aminoiminomethyl)amino]butyl]-1-[N-(methylsulfonyl)-D-phenylalanyl]-L-prolinamide, trifluoroacetate (1:1) salt

A.

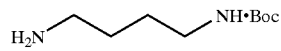

To a stirred solution of 1,4-diaminobutane (50 g, 567 mmol) in 195 mL of dioxane under argon at room temperature was added dropwise a solution of di-t-butyl dicarbonate (15.7 g, 71.9 mmol) in 195 mL of dioxane over 3.5 h. Some white precipitate appeared during the addition. The mixture was stirred at room temperature for 22 h and concentrated in vacuo. The residue was diluted with 320 mL of water and the precipitate was filtered off. The aqueous filtrate was extracted with methylene chloride (3×300 mL). The combined methylene chloride extracts were washed in water (2×200 mL) and brine (1×200 mL). The organic layer was dried (MgSO$_4$), filtered and concentrated in vacuo to give 9.79 g (72%) of title mono-BOC.amine.

B.

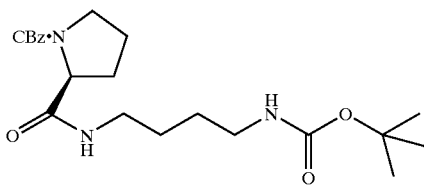

To a stirred solution of N-CBz-L-proline (12.7 g, 50.9 mmol), 1-hydroxybenzotriazole monohydrate (6.49 g, 50.9 mmol) and Part A BOC.amine (9.57 g, 50.9 mmol) in 250 mL of DMF was added in order 4-methylmorpholine (11.2 mL, 102 mmol) and ethyl-3-(dimethylamino) propyl carbodiimide hydrochloride (9.76 g, 50.9 mmol). The reaction solution was stirred at room temperature for 22 h and concentrated under pump vacuum at 50° C. The residue was diluted with 600 mL of EtOAc and washed with 1N HCl solution (2×250 mL), saturated NaHCO$_3$ solution (2×250 mL) and brine (1×250 mL). The EtOAc layer was dried (MgSO$_4$), filtered and concentrated in vacuo to give 20.7 g (97%) of title CBz.amine.

C.

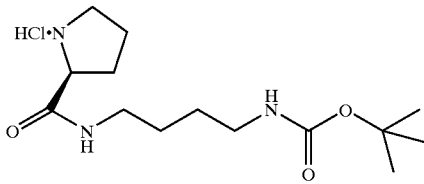

To a stirred solution of Part B CBz.amine (20.2 g, 48.2 mmol) in 250 mL of methanol under argon was added 20% Pd(OH)$_2$/C (4.04 g, 20% based on the weight of Part B amine). The atmosphere was replaced by hydrogen with several vacuum-fill cycles. The reaction mixture was stirred at room temperature for 21 h. The catalyst was filtered off through a 4 μM polycarbonate film and rinsed with methanol (3×50 mL). The filtrate was concentrated in vacuo. The oily residue was dissolved in 200 mL of ether and treated with 1N HCl solution in ether (53.0 mL 53.0 mmol). The solution was concentrated in vacuo. The residue was mixed with 300 mL of toluene and 30 mL of methanol and concentrated in vacuo to give title amine hydrochloride in a quantitative yield (15.5 g) as an oil.

D.

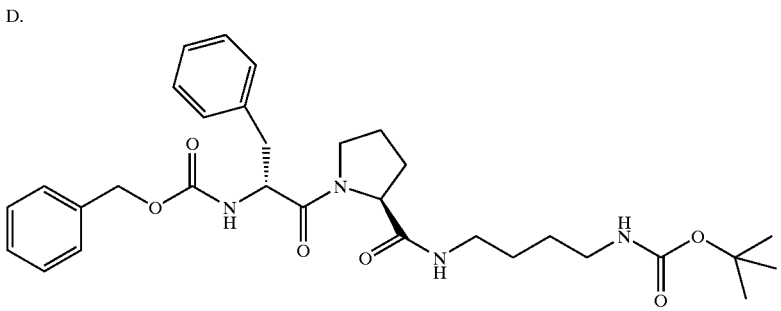

A stirred solution of N-α-CBZ-D-phenylalanine (0.56 g, 1.9 mmol) in 6.5 mL of DMF at room temperature under argon was treated with 1-hydroxybenzotriazole (0.29 g, 1.9 mmol) and EDAC* (0.36 g, 1.9 mmol). After 20 minutes, Part C compound was added (0.50 g, 1.6 mmol) and stirring was carried out for 16 hours. The reaction was quenched by the addition of 75 mL of 0.25M KHSO$_4$ solution. The suspension was washed with EtOAc (2×40 mL), the combined EtOAc layers were washed with 0.25M KHSO$_4$ solution (2×40 mL), saturated aqueous KHCO$_3$ solution (2×40 mL), brine, dried (Na$_2$SO$_4$), and concentrated to yield 1.07 g of a white taffy, which by TLC analysis appeared to contain unreacted N-α-CBZ-D-phenylalanine. The crude product was redissolved in 60 mL of EtOAc, washed with saturated aqueous KHCO$_3$ solution (3×40 mL), brine, dried (Na$_2$SO$_4$), concentrated, co-evaporated several times with ether and hexane and triturated with 50 mL of hexane to yield title compound (0.78 g, 88%) as a colorless solid.

E.

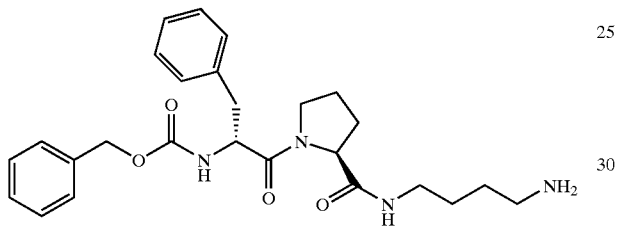

Trifluoroacetic acid (3.2 mL) was added to ice-cooled Part D compound (0.78 g, 1.4 mmol). The reaction solution was stirred at room temperature for 2 hours and 45 minutes. Trifluoroacetic acid was removed under vacuum and co-evaporated several times with ether and hexane to obtain a colorless taffy.

F.

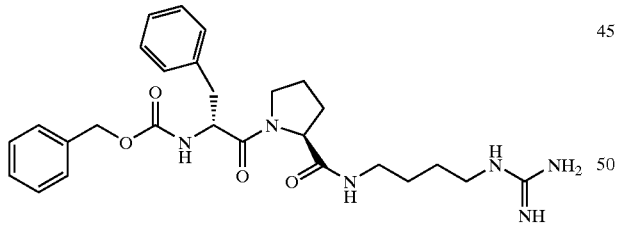

A solution of Part E compound (0.80 g, 1.38 mmol) in 10.9 mL of absolute ethanol was treated with amidine sulfonic acid (0.26 g, 2.1 mmol) followed by triethylamine (0.58 mL, 4.1 mmol). After addition of the triethylamine, a yellow, homogeneous reaction solution slowly formed. After 2 hours, TLC analysis of the reaction mixture indicated it was complete. The reaction mixture was concentrated, dissolved in 25 mL of CH$_3$OH, and filtered. Preparative HPLC of the filtered solution provided the title compound as a colorless solid, (414.0 mg, 45%) mp 50–140° C. with foaming.

G.

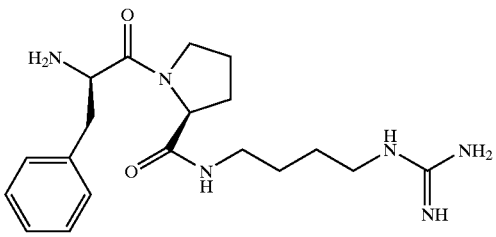

A solution of 0.20 g (0.30 mmol) of Part F compound in 1.5 mL of CH$_3$OH with 40 mg of Pearlman's catalyst was hydrogenated at 1 atm for 3 hours. The reduction was judged complete by TLC analysis after 2.5 hours. The catalyst was removed by filtration and the filtrate was concentrated to yield an oil, which was redissolved in 10 mL of CH$_3$OH, acidified with 0.20 mL of trifluoroacetic acid, concentrated, dissolved in H$_2$O and lyophilized to yield title compound as a colorless solid (152.1 mg, 81%), mp 124–125° C.

H. N-[4-[(Aminoiminomethyl)amino]butyl]-1-[N-(methylsulfonyl)-D-phenylalanyl]-L-prolinamide, trifluoroacetate (1:1) salt

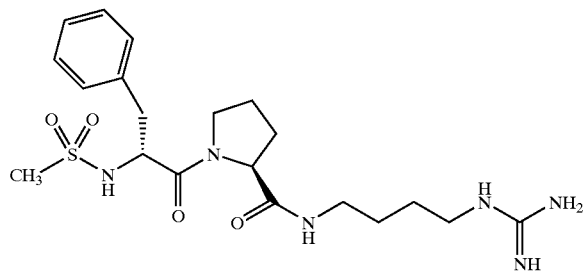

To a stirred solution of Part H compound (550 mg, 0.80 mmol) in 15 mL of dry CH$_2$Cl$_2$ and 15 mL of dry THF under argon was added Et$_3$N (0.44 mL, 3.20 mmol) followed by methanesulfonyl chloride (68.0 μL, 0.88 mmol). The turbid mixture was stirred at room temperature for 3 h and diluted with 0.50 mL of water. The mixture was stirred at room temperature for 10 min and concentrated in vacuo, the residue diluted with 30 mL of methanol and concentrated in vacuo. This material was purified by preparative HPLC and lyophilized to give 300 mg (75%) of title compound.

Analysis for 1.15 CF$_3$COOH+0.75 H$_2$O: C, 44.85; H, 5.85; N, 14.07; S, 5.37; F, 10.97

Found: C, 45.02; H, 5.82; N, 13.94; S, 5.34; F, 10.89

Optical rotation: $[\alpha]_D = -73.2°$ (c=1.00, MeOH)

Following the procedures of Example 1, the following examples of compounds of the invention may be prepared.

TABLE

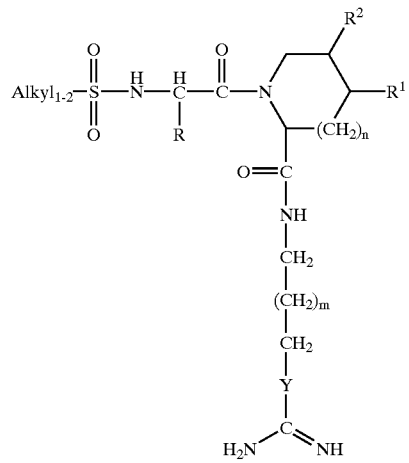

| Example No. | Alkyl$_{1-2}$ | R | R$^2$ | R$^1$ | n | m | Y |
|---|---|---|---|---|---|---|---|
| 2 | C$_2$H$_5$ | CH$_2$OH(S) | H | H | 1 | 2 | NH |
| 3 | CH$_3$ | H | OH | H | 0 | 1 | NH |
| 4 | C$_2$H$_5$ | —CH$_2$C$_6$H$_5$(R) | OCH$_3$ | CH$_3$ | 0 | 2 | S |
| 5 | CH$_3$ | —CH$_2$C$_6$H$_5$(S) | | | | | |
| 6 | C$_2$H$_5$ | —CH$_2$CH$_2$CONH$_2$(S) | H | H | 1 | 0 | S |
| 7 | CH$_3$ | —CH$_2$CH$_2$CONH$_2$(R) | H | CH$_3$ | 1 | 1 | NH |
| 8 | C$_2$H$_5$ | —CH(OH)CH$_3$(S-Thr) | —CHCH$_2$CH$_2$CH— | | 0 | 2 | S |
| 9 | CH$_3$ | CH(OH)CH$_3$(S-alloThr) | CH$_3$ | H | 1 | 2 | NH |
| 10 | C$_2$H$_5$ | 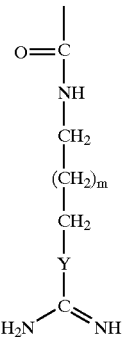 (R) | SCH$_3$ | CH$_3$ | 1 | 1 | S |
| 11 | CH$_3$ | —CH$_2$CH$_2$CO$_2$H(R) | H | CH$_3$ | 0 | 3 | NH |
| 12 | C$_2$H$_5$ | CH$_2$OCH$_2$Ph(R) | H | H | 1 | 0 | S |
| 13 | CH$_3$ | CH$_2$CH$_2$Ph(s) | H | H | 1 | 1 | NH |

What is claimed is:

1. A compound having the structure

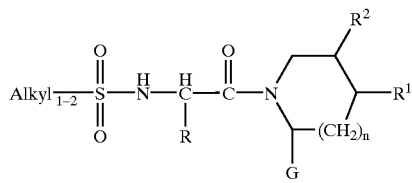

including all stereoisomers, wherein n is 0, 1 or 2;

G is an amido moiety of the structure wherein m is 0, 1, 2 or 3; and

Y is NH or S;

R is hydrogen, hydroxyalkyl, aminoalkyl, alkyl, cycloalkyl, arylalkyl, alkenyl, alkynyl, amidoalkyl, arylalkoxyalkyl or an amino acid side chain, either protected or unprotected;

$R^1$ and $R^2$ are independently hydrogen, lower alkyl, cycloalkyl, aryl, hydroxy, alkoxy, oxo, thioxo, thioalkyl, thioaryl, amino or alkylamino; and $Alkyl_{1-2}$ is methyl or ethyl;

unless otherwise indicated, the term "alkyl" alone or as part of another group refers to straight and branched chain radicals of up to 18 carbons;

the term aryl alone or as part of another group refers to monocyclic or bicyclic aromatic groups;

or a pharmaceutically acceptable salt thereof.

2. The compound as defined in claim 1 having the structure

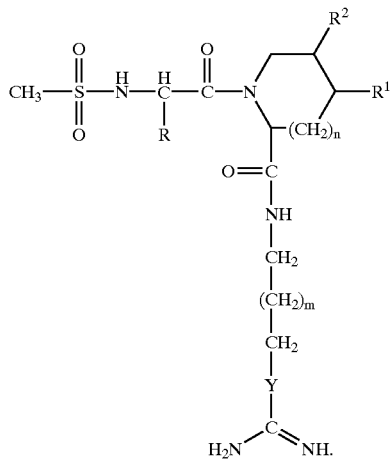

3. The compound as defined in claim 2 wherein n is 1 and m is 2, R is hydroxyalkyl or aralkyl, $R^1$ is H or alkyl, $R^2$ is H and Y is —NH—.

4. The compound as defined in claim 1 having the structure

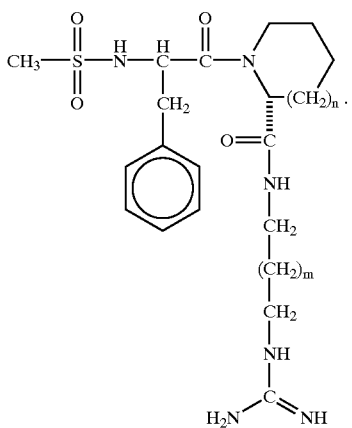

5. The compound as defined in claim 1 which is N-[4-[(aminoiminomethyl)amino]butyl]-1-[N-(methylsulfonyl)-D-phenylalanyl]-L-prolinamide, or a salt thereof including its trifluoroacetate salt.

6. The compound as defined in claim 1 which is N-[4-[(aminoiminomethyl)amino]butyl]-1-[N-(ethylsulfonyl)-D-phenylalanyl]-L-prolinamide, or a salt thereof including its trifluoroacetate salt.

7. A method of inhibiting or preventing formation of blood clots, which comprises administering to a patient in need of treatment a therapeutically effective amount of a compound as defined in claim 1.

* * * * *